(12) United States Patent
Flyash et al.

(10) Patent No.: US 8,516,706 B2
(45) Date of Patent: Aug. 27, 2013

(54) SKIN-HEATING SHAVING APPARATUS AND METHOD

(75) Inventors: Lion Flyash, Nazareth-Illit (IL); Shimon Eckhouse, Haifa (IL)

(73) Assignee: Syneron Medical Ltd, Yokneam (IL)

( * ) Notice: Subject to any disclaimer, the term of this patent is extended or adjusted under 35 U.S.C. 154(b) by 466 days.

(21) Appl. No.: 12/684,381

(22) Filed: Jan. 8, 2010

(65) Prior Publication Data

US 2011/0167640 A1 Jul. 14, 2011

(51) Int. Cl.
*B26B 21/48* (2006.01)

(52) U.S. Cl.
USPC .............................. 30/34.05; 30/32

(58) Field of Classification Search
USPC .................... 30/34.05, 50, 32
See application file for complete search history.

(56) References Cited

U.S. PATENT DOCUMENTS

| | | | | |
|---|---|---|---|---|
| 2,888,927 A * | 6/1959 | Fozard | | 606/43 |
| 3,364,568 A * | 1/1968 | Lowy | | 30/34.05 |
| 4,174,713 A * | 11/1979 | Mehl | | 606/42 |
| 4,185,632 A * | 1/1980 | Shaw | | 606/31 |
| 4,566,454 A * | 1/1986 | Mehl et al. | | 606/36 |
| 4,823,813 A * | 4/1989 | Harrison | | 607/101 |
| 5,049,148 A * | 9/1991 | Mehl | | 606/43 |
| 5,125,928 A * | 6/1992 | Parins et al. | | 606/48 |
| 5,394,777 A * | 3/1995 | Kozikowski | | 83/15 |
| 5,771,589 A * | 6/1998 | Kim | | 30/346.58 |
| 5,846,252 A * | 12/1998 | Mehl, Sr. | | 606/133 |
| 6,014,918 A * | 1/2000 | Orloff | | 83/13 |
| 6,159,222 A * | 12/2000 | Yiu | | 606/133 |
| 6,463,661 B2 * | 10/2002 | Skipper | | 30/74 |
| 6,472,062 B1 * | 10/2002 | Neerinck et al. | | 428/336 |
| 6,533,775 B1 * | 3/2003 | Rizoiu | | 606/9 |
| 6,544,259 B1 * | 4/2003 | Tsaliovich | | 606/36 |
| 6,620,158 B2 * | 9/2003 | Ronci | | 606/36 |
| 6,629,974 B2 * | 10/2003 | Penny et al. | | 606/41 |
| 6,817,101 B1 * | 11/2004 | Bohmer | | 30/34.05 |
| 6,836,966 B2 * | 1/2005 | Patrick | | 30/34.05 |
| 7,238,183 B2 * | 7/2007 | Kreindel | | 606/41 |
| 7,367,126 B2 * | 5/2008 | Freund et al. | | 30/41.7 |
| 7,654,003 B2 * | 2/2010 | Simms et al. | | 30/34.05 |
| 7,996,994 B2 * | 8/2011 | Trezon | | 30/34.05 |
| 2007/0239152 A1 * | 10/2007 | Trezon | | 606/36 |
| 2009/0000123 A1 * | 1/2009 | Trezon | | 30/34.1 |
| 2010/0024615 A1 * | 2/2010 | Rebaudieres et al. | | 83/14 |
| 2010/0031510 A1 * | 2/2010 | Gester et al. | | 30/34.05 |
| 2011/0016721 A1 * | 1/2011 | Schnak et al. | | 30/34.05 |
| 2011/0167640 A1 * | 7/2011 | Flyash et al. | | 30/34.05 |
| 2012/0116271 A1 * | 5/2012 | Caruso et al. | | 601/6 |
| 2012/0143178 A9 * | 6/2012 | Mehta | | 606/33 |
| 2012/0143270 A1 * | 6/2012 | Mehta | | 607/2 |

\* cited by examiner

*Primary Examiner* — Sean Michalski

(74) *Attorney, Agent, or Firm* — Smith Risley Tempel Santos LLC; Gregory Scott Smith

(57) ABSTRACT

A shaver that includes a cartridge with one or more razor blades and a source of RF energy operative to apply RF energy to one or more of the blades. The cartridge can be attached to a handle for moving the cartridge along the surface of the skin. The cartridge may include a variety of configurations including one or more electrodes and one or more blades with the RF current conducting through any subset of the electrodes and blades, through the skin, thereby heating the skin to help facilitate the engagement of the blade with the hair on the skin surface.

14 Claims, 11 Drawing Sheets

FIG. 5B
AXIS Z-Z
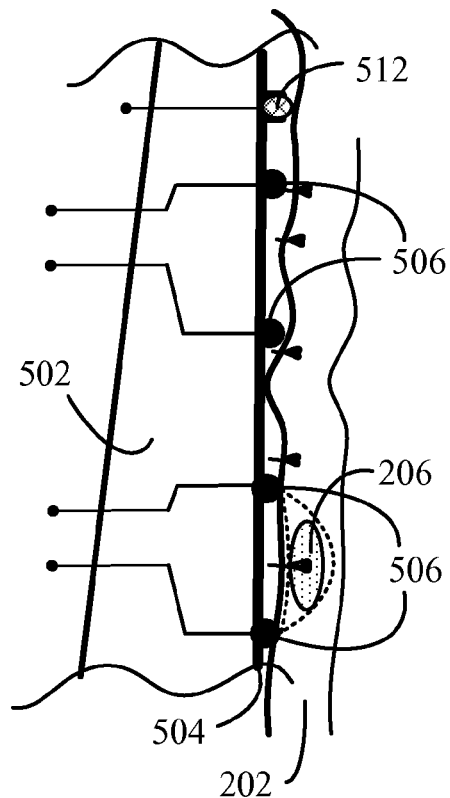
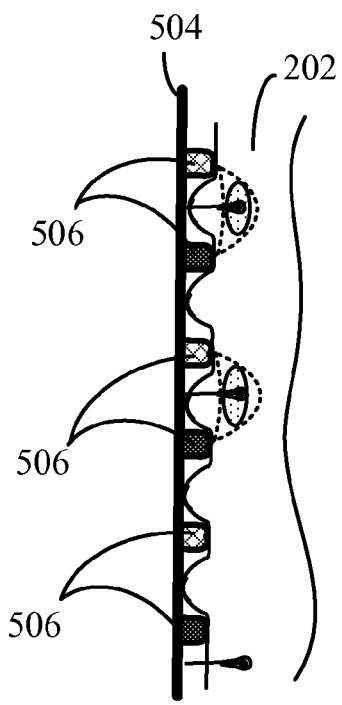
AXIS W-W
FIG. 5C

SKIN-HEATING SHAVING APPARATUS AND METHOD

CROSS-REFERENCE TO RELATED APPLICATIONS

This application is related to and incorporates by reference U.S. patent application Ser. No. 12/324,932 filed on Nov. 28, 2008.

TECHNICAL FIELD

The method and apparatus relate to shaving razors and in particular to razors operative to apply RF heating energy to skin during shaving.

BACKGROUND

Several attempts have been made in the art to reduce the discomfort and irritation resulting from shaving while still allowing for a close shave, i.e. leaving a hair stub as short as possible, preferably having the remaining hair shaft tip rest inside the hair follicle, so that the shaved skin is smooth to the touch.

Multiple blade cartridges, fixed to, or pivot about their handle, such as Gillette brand Sensor Excel™ series, employ the hair pulling-and-cutting process. The process includes a set of "resiliently mounted elements" such as that described in U.S. Pat. No. 5,802,721 or a blade which lifts the hair up, pulling it as far out of the skin follicle as possible, so that the cutting operation is performed by a succeeding blade on the part of the hair that is, when relaxed, below the surface of the skin. This process may sometimes be associated with discomfort resulting from the stiffness of the hairs and the tugging applied to the hair shaft that is strongly attached to the follicle in which it is situated.

In an attempt to minimize the discomfort resulting from the pulling and cutting process, it has become common practice to heat the razor blades and/or facial skin with hot water so as to soften the hair bristles. Shaving creams, gels and lotions have also been developed for the same reason.

Some shaving devices known in the art set out to reduce the discomfort of pulling-on and cutting stiff hairs by heating the device itself. The idea shared by most is heating the cartridge blades employing means other than rinsing with hot water. United States patent application 2006/0117568 describes pre-heating of the razor cartridge prior to shaving and relying on heat conduction to warm the blades. Other shaving devices, such as that described in U.S. Pat. No. 6,836,966 and U.S. Pat. No. 6,817,101, electrically heat the blades themselves in an attempt to soften the hair shafts.

BRIEF SUMMARY

In accordance with one exemplary embodiment of the current method and apparatus, a shaver is provided having a cartridge including one or more razor blades and a source of RF energy operative to apply RF energy to one or more of the blades. Further, such embodiment may include a handle that can be held or gripped to enable maneuverability of the cartridge over the surface of the skin. The one or more blades are operative to couple the RF energy to the skin.

Applying RF energy to the skin operates to heat the skin, soften the hair shaft and in some cases affect the hair follicle so that to reduce the discomfort resulting from the stiffness of the hairs and the tugging. Advantageously, these characteristics help to make the shaving process more pleasant and soothing from the perspective of a user and, to provide a closer shave with minimal irritation to the skin.

In accordance with another embodiment of the current method and apparatus the cartridge includes one or more razor blades and one or more RF electrodes.

Acne is one of the most common skin disorders and is affecting millions of people. In accordance with yet another embodiment of the current method and apparatus, the heat generated at deeper levels of the skin, such as at the level of the dermis, for example, is sufficient to inactivate *Propionibacterium acnes* (*P. acnes*) bacteria commonly located therewithin, thus assisting in the healing process of existing facial acne and preventing future development thereof.

Optionally, in accordance with still another embodiment of the current method and apparatus, the cartridge may also include one or more blades constructed of a high electrical—resistance material that may generate additional heat when necessary. The cartridge may also include a heat sensor, such as a thermistor and an electronic control to control and/or regulate the temperature of the skin, blades or electrodes. The heat sensors may be located on the cartridge itself, blades and/or electrodes.

The blades may also be coated with one or more types of coating such as a protective coating, thermally conductive coating, hardness increasing coating, dielectric coating and a coating reducing blade friction.

In accordance with another embodiment of the current method and apparatus the blades may be cooled by a heat sink or other cooling means to protect the surface of the skin when heating deeper layers thereof. This results in the heat generated by the RF energy in the skin to be specifically directed, if so desired, at the level of the hair follicles in addition to softening the hair shafts or any other desired level. Additionally or alternatively the heat generated by the RF energy in the skin may be specifically directed at the collagen layer bringing about stimulation and growth thereof. These applications of RF energy to the skin of the user (and in particular to the facial area.) may also contribute to changes in deeper skin layers that may bring about wrinkle reduction, tightening of the skin and an overall enhanced comfort during shaving.

It will be appreciated that the energy applied by the aforementioned electrodes may be replaced by other heat energy generating means such as light energy, ultrasound energy and others.

BRIEF DESCRIPTION OF THE DRAWINGS

The present method and apparatus will be understood and appreciated from the following detailed description, taken in conjunction with the drawings in which:

FIGS. 5A, 5B and 5C are simplified illustrations of yet another exemplary embodiment of the current method and apparatus.

DETAILED DESCRIPTION

The term "Skin", as used in the present disclosure, means all layers of skin including the epidermis, dermis including all dermal structures such as hair follicles, blood vessels, collagen tissue and the fat layer.

Figure 1:
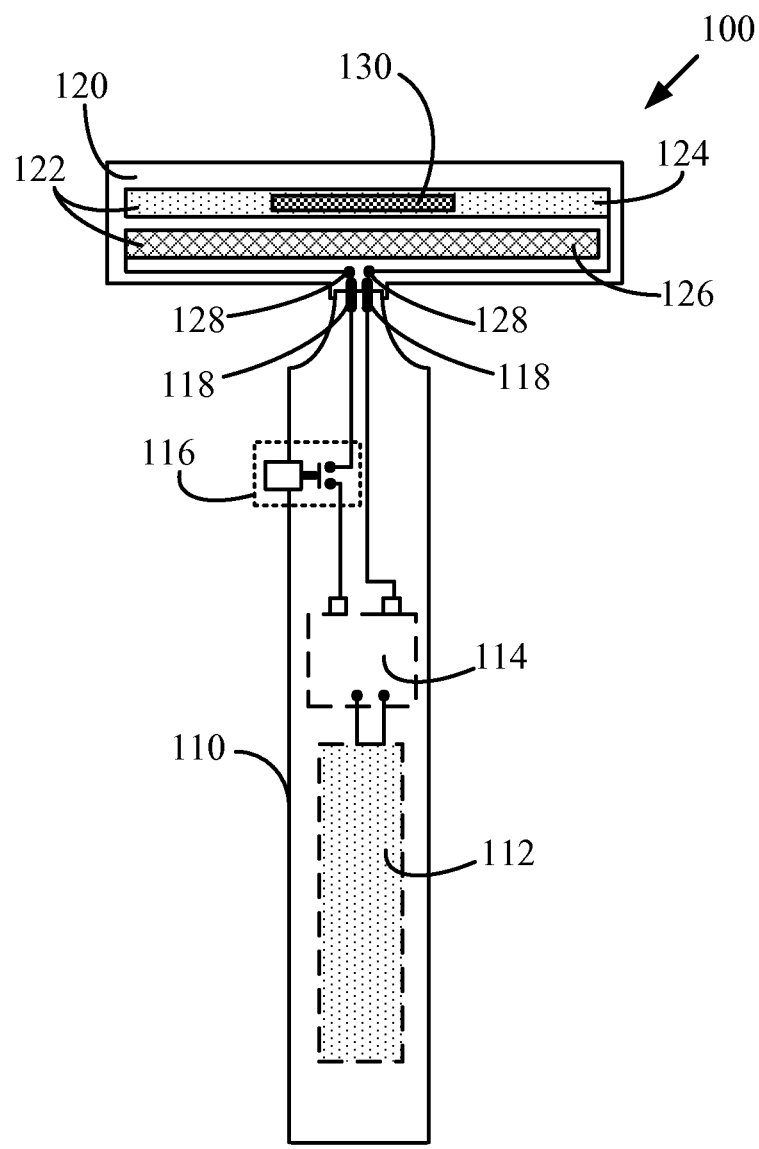
FIG. 1 is a simplified illustration of a shaving apparatus constructed and operative in accordance with an exemplary embodiment of the present apparatus and method.

Reference is now made to FIG. 1, which is a simplified illustration of a shaving apparatus constructed and operative in accordance with an exemplary embodiment of the present apparatus and method. A shaving apparatus 100 includes a handle 110 that can be held or gripped and a reusable or disposable cartridge 120 that can be attached, coupled, joined, and/or connected, and sealed to the handle 100 in such a way as to prevent penetration of water into the handle, but that can also be removed again from the handle.

The handle 110 includes or houses a source of energy 112 operative to supply energy to an RF generator 114, which, in turn, supplies RF energy to the components in cartridge 120, such as RF coupling blades, electrodes, gel dispenser heating elements 420 (FIGS. 4D and 4E) etc. The level and duration of the RF energy supply to cartridge 120 components is controlled by a control circuit 116. Control circuit 116 may be operational intermittently upon demand, such as (a) a pressable bias-countered switch, (b) an adjustable type control to adjust the level of desired RF power output or (c) a standard on-off type switch as known in the art. The handle 110 also includes terminals 118 located at the attachable tip thereof, which come in contact with corresponding terminals 128 located at the attachable portion on cartridge 120 upon attachment thereof to handle 110. The RF power may be generated in continuous or pulse form, a variation or combination of both, and can vary in the range in the amount or duration of the continuous power, or the duty cycle and frequency of the pulsed power.

In another embodiment of the current method and apparatus, either one or both of power source 112 and RF generator 114 may be located externally to handle 110 and supply the power or RF signals to the handle 110 through an electrical cord (not shown). Control circuit 116 in this embodiment may be located on handle 110 or on a housing (not shown) in which power source 112 and/or RF generator 114 may be located.

Cartridge 120 may include, among other components, one or more blades, a pair of which 122 is presented in FIG. 1. Cartridge 120 may be disposable in part or en-bloc. Blades 122 are positioned in parallel to each other and are operative to cut hair and couple RF energy to the skin while translating cartridge 120, employing handle 110, in a stroking motion over the skin to be shaved. Blades 122 may be supplied with RF energy from RF generator 114 of handle 110 with which they electrically communicate through terminals 128 and 118.

In an exemplary embodiment of the current method and apparatus the electrical wiring of blades 124 and 126 may be configured as depicted in FIG. 1 so that blades 124 and 126, when supplied with RF energy from RF generator 114 create an RF current that flows between the blades, as will be explained in further detail below. In other exemplary embodiments of the current method and apparatus either one, or both, of blades 124 and 126 may be replaced by an RF electrode.

Blades 124 and 126 may also be coated with one or more types of coating such as a protective coating, thermally conductive coating, hardness increasing coating, dielectric coating and/or a coating that reduces the blade friction. Additionally or alternatively, blades 124 and 126 may be constructed of a highly electrical resistance material to enable the blades to generate heat when a current is passed through the blades.

In accordance with yet another embodiment, blades 124 and/or 126 may also include a thermistor 130 to monitor and/or control and/or regulate the temperature of the skin being shaved.

Figure 2A:
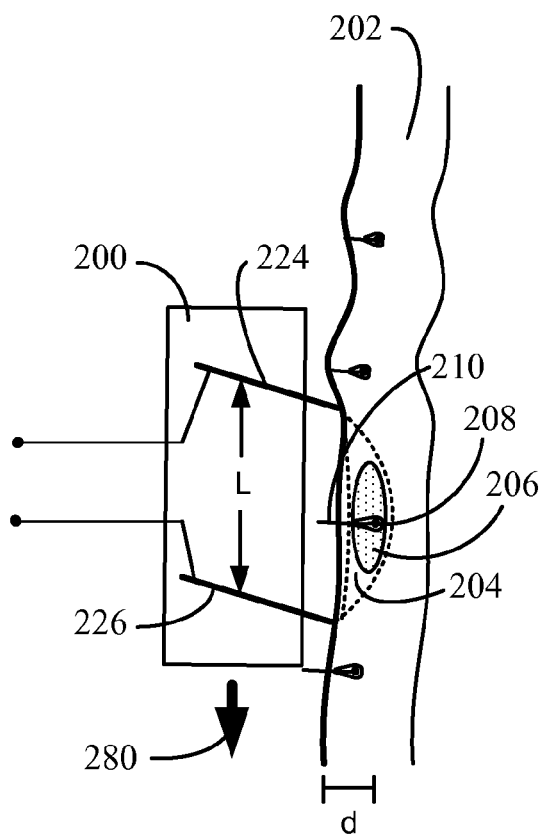
FIGS. 2A, 2B, 2C, 2D, 2E and 2F are simplified cross-sectional view illustrations of four exemplary embodiments of current method and apparatus.
Figure 2B:
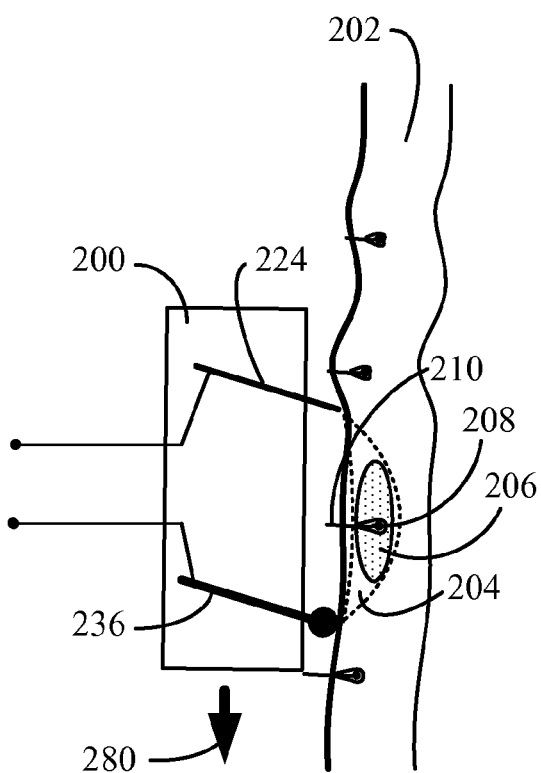

Turning now to FIGS. 2A and 2B, which are simplified cross-sectional view illustrations of two exemplary embodiments of the current method and apparatus. FIG. 2A illustrates a double blade configuration in which reusable or disposable cartridge 200 includes blades 224 and 226, operative to couple RF energy to skin 202 to be shaved. Blades 224 and 226, when supplied with RF energy, create a current 204 that flows from one blade, through skin 202 and to the other blade. Current 204 causes the heating of a skin portion 206 that, for purposes of this exemplary embodiment only, is located in the dermis layer of skin 202 at the level of, and including but not limited to, hair follicle 208 and hair 210. The heat generated in skin portion 206 of skin 202 softens hair shaft 210 making it more amenable to cutting by blade 224 when cartridge 200 is translated over the skin in the direction depicted by arrow 280. Additionally, applying RF energy to skin 202 sometimes allows detachment of the hair shaft 210 from follicle 208 as well as affecting the follicle itself in some cases.

The depth (d) of heated portion 206 from the surface of the skin may be determined by the level of RF power coupled by blades 224 and 226 and the distance (L) between the two blades. For example, at a given RF setting, the depth (d) of heated portion 206 is approximately half of the distance (L) between blades 224 and 226. However, those skilled in the art will appreciate that this ratio can vary depending on a variety of factors including the material used in the blades, the frequency of the RF energy, the type of skin and the chemical composition of the skin as well as materials (lotions, sweat, water, etc.) on the surface of the skin 202. Assuming, for purpose of example only, that the thickness of skin 202 to be shaved is approximately 1.8 mm, to achieve heating of hair follicles 208 in skin 202, the desired center of heated portion 206 should be located at an approximate depth (d)=of 0.9 mm. This requires positioning blades 224 and 226 with a distance (L)=1.8 mm between the blades. The depth of heated segment 206 may, when so desired, also affect the sub-cutaneous fatty tissue layer (not shown). In general, the higher the level of RF power coupled to the skin—the higher the resulting temperature of heated portion 206. Heat effected in the center of portion 206 is carried outward in a radial fashion by conduction, heating adjoining portions and enlarging the volume of portion 206.

Shaving other areas of the body having thicker skin resulting from a thick dermis layer or deeper collagen layer may require readjusting the level of coupled RF energy or the distance between blades 224 and 226. The coupled RF power levels may range from, but not be limited to, 1-20 Watts. The RF frequency may range from, but not be limited to, 300 kHz to 10 Mhz.

The heat generated by coupled RF energy to skin 202 may bring about additional beneficial changes in the tissue, such as the breakdown of collagen fibers in the dermis and stimulation of collagen tissue resulting in wrinkle reduction, tightening of the skin as well as overall enhanced comfort during shaving.

In another embodiment of the current method and apparatus the level of heat generated by coupled RF energy to skin 202 may be selected to reach a temperature in a range known to deactivate *Propionibacterium acnes* (*P. acnes*) bacteria, the cause of facial acne. It has been demonstrated that the application of heat at various time and temperature combinations reliably deactivates the *P. acnes* bacteria. The necessary temperature range to deactivate the *P. acnes* bacteria is generally above 47 degrees Celsius, but below the burn or discomfort threshold for human skin. Depending on the area of skin and the area of surface contact, the upper discomfort threshold is in the range of 51 degrees Celsius. Hence, coupling RF energy employing a relatively rapid, transient application such as shaving strokes may bring about transient heating of skin 202 portion 206, to temperatures necessary to deactivate *P. acnes* bacteria within the portion 206. Additionally, heating the skin also increases the blood circulation in the heated area. This not only assists in the healing process of existing facial acne but may also assist in preventing future acne development since *P. acnes* is a common resident (commensal) in human skin. Cooling the surface of the skin, as will be described in greater detail below, may increase tolerability to increased *P. acnes* bacteria deactivation temperatures in the skin in general and in deeper layers specifically.

Referring now to FIG. 2B, which is a simplified cross-sectional view illustration of another exemplary embodiment of the shaving apparatus of FIG. 1. In this embodiment, blade 226 of FIG. 2A is replaced by electrode 236, which may be an RF electrode. Electrode 236 may be rounded, coated with a smooth-surface material, in a form of a roller or in any other form which enables electrode 236 to be operative to translate smoothly over the surface of the skin.

Figure 2C:
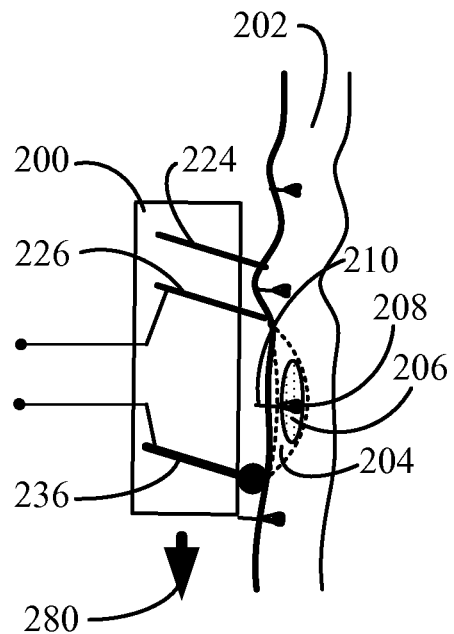
Figure 2D:
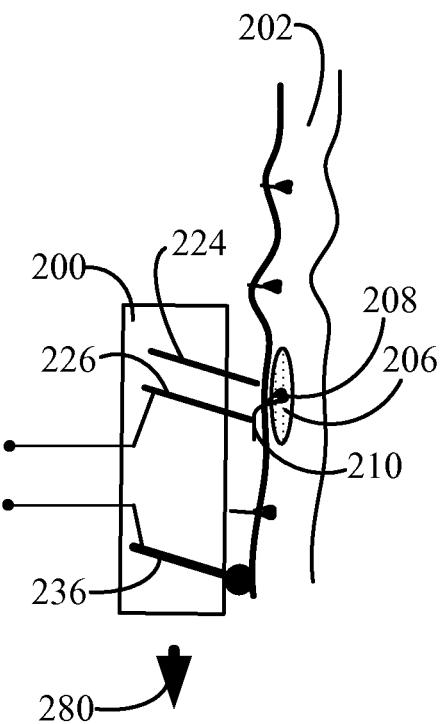
Figure 2E:
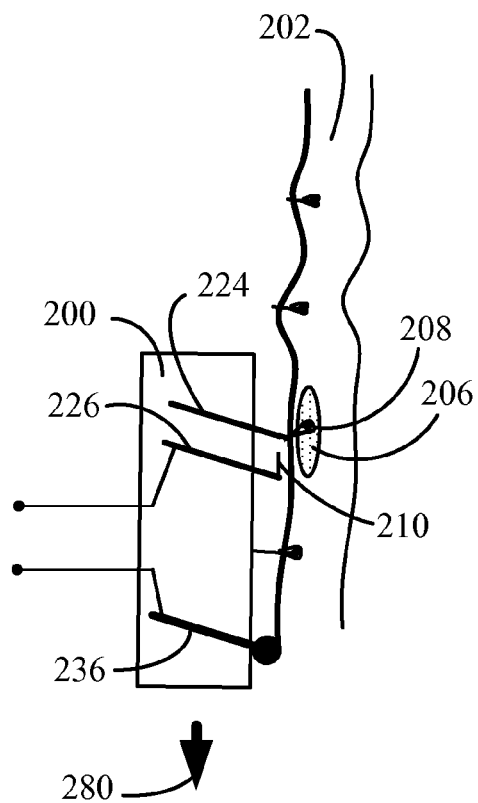

Referring now to FIGS. 2C, 2D and 2E which are simplified cross-sectional view illustrations of yet another exemplary embodiment of the current method and apparatus. FIG. 2C depicts a cartridge 200 including 2 blades 224 and 226 and an electrode 236. Alternatively, electrode 236 may be replaced by a blade and either one of blades 224 and 226 may be replaced by an RF electrode. The distance between blade 226 and electrode 236 is selected to generate the heating of portion 206 of skin 202 and hair follicle 208 as described hereinabove. The distance between blades 224 and 226 is selected to enable the engagement with hair on the skin surface, such as the pulling the hair, cutting the hair, and/or the pulling-and-cutting process as employed by Gillette brand Sensor Excel™ series and other multiple blade shaving cartridges and as described in U.S. Pat. No. 5,802,721. In FIG. 2C, RF energy is coupled to skin 202 generating heat in heated portion 206 heating hair follicle 208 and hair shaft 210. This softens hair shaft 210 making the hair more prone to be cut or removed. FIG. 2D depicts translation of cartridge 200 over the surface of the skin in a direction depicted by arrow 280. At this stage, coupling of RF energy to skin 202 may cease (e.g., in RF pulse mode) or be applied continuously to go on heating another portion of skin. Blade 226 catches hair shaft 210 and partially pulls it out of follicle 208. At this point in time, hair shaft 210 may be softer and its attachment to follicle 208 more resilient, having been heated by RF energy coupled thereto, making hair shaft 210 readily movable within follicle 208. This further reduces the pain and discomfort associated with the shaving process. FIG. 2E illustrates further translation of cartridge 200 over the skin in the direction depicted by arrow 280 bringing about cutting of the now softened and pulled hair shaft 210 by blade 224. Alternatively, the temperature reached within heated portion 206 may sometimes bring about changes in follicle 208 resulting in easier removal of hair shaft 210 upon pulling thereof from follicle 208 at the stage depicted by FIG. 2D.

The temperature achieved in the skin and over the surface thereof and the amount of resistance of the hair to pulling and detachment from the hair follicle may be dependent not only on the type of electrode, type of applied charge wave (i.e., pulsed or continuous), level and duration of the RF voltage and distance between the electrodes, but also on the speed of translation of cartridge 200 over the skin.

Figure 2F:
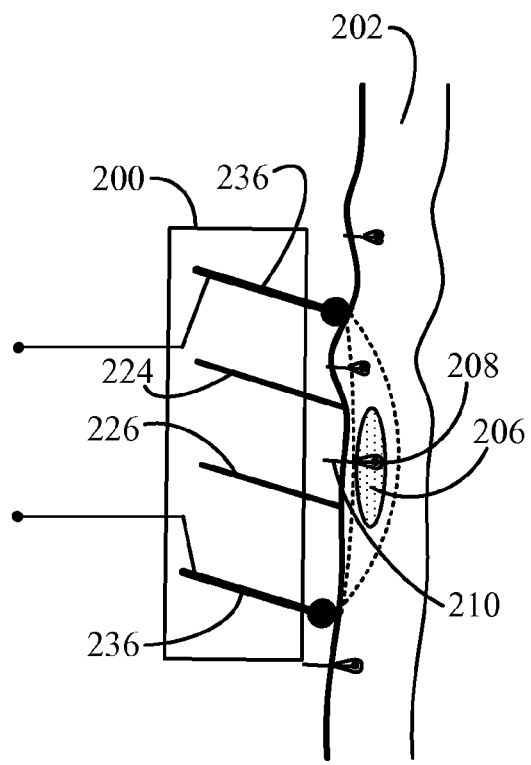

Referring now to FIG. 2F, which is a simplified cross-sectional view illustration of yet another exemplary embodiment of current method and apparatus. In this embodiment, cartridge 200 includes two marginally located electrodes 236 and having blades 224 and 226 located between the electrodes. In this configuration, blades 224 and 226 may be rotating blades such as those employed by electrically motorized shaving devices, standard blades, reciprocating blades, vibrating blades, etc.

Figure 3A:
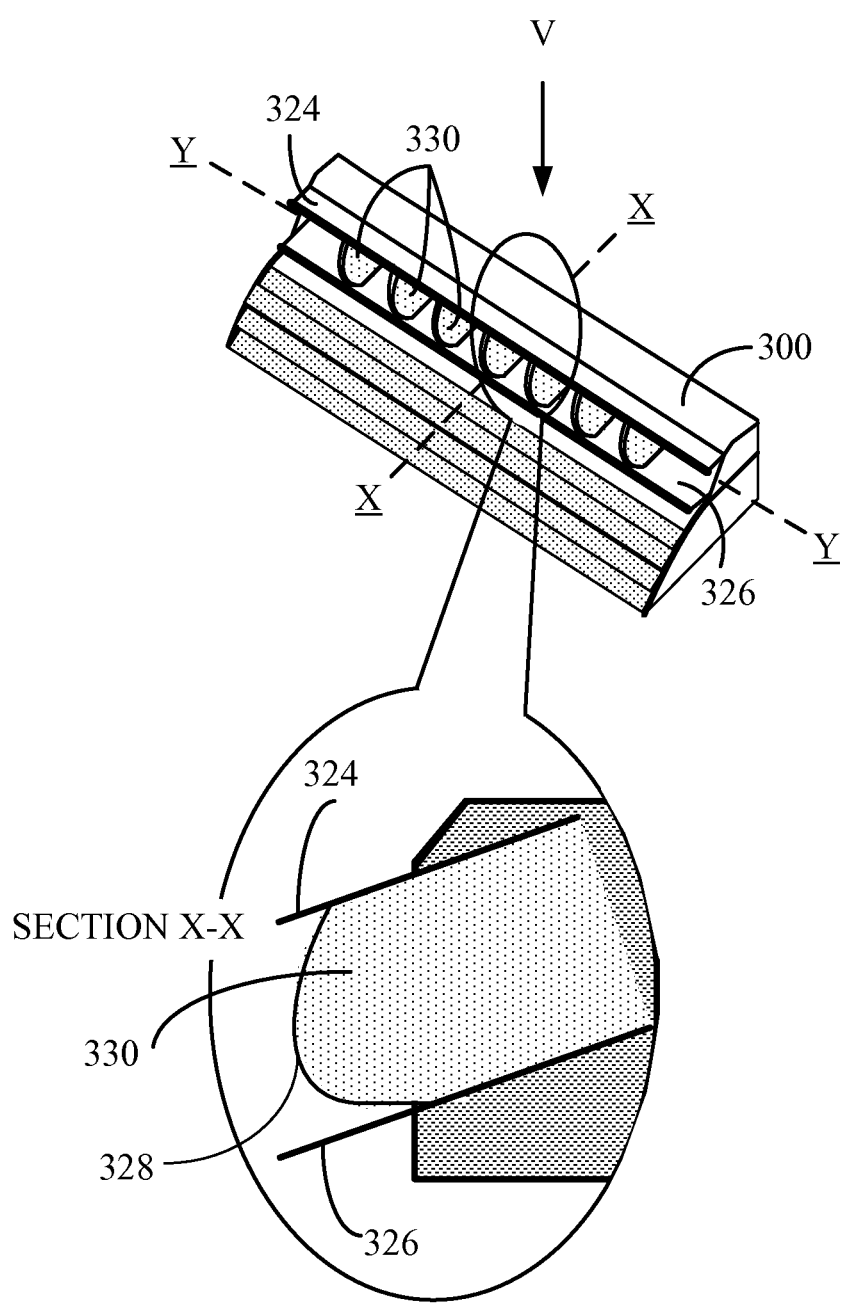
FIG. 3A is a simplified elevated oblique view and sectional cross-section view illustration of another exemplary embodiment of the current method and apparatus.
Figure 3B:
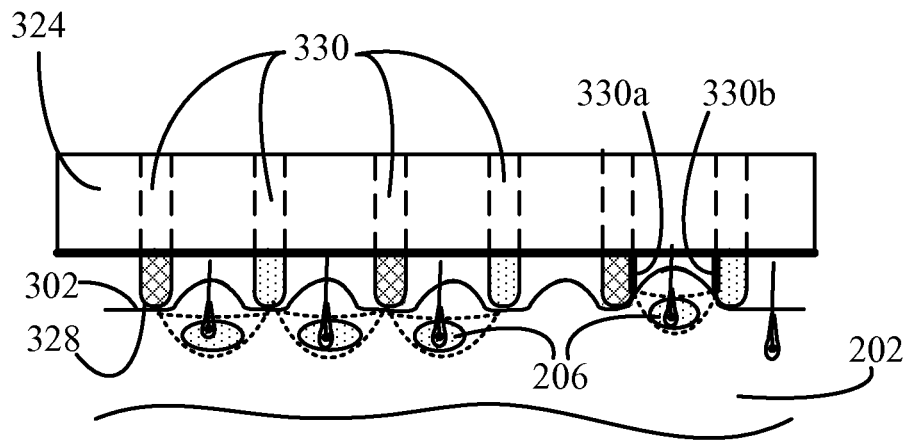
FIG. 3B is a simplified cross-sectional view illustration of the shaving apparatus of FIG. 3A as viewed in the direction indicated by arrow (V)

Turning now to FIG. 3A, which is a simplified elevated oblique view and sectional cross-section view illustration of another exemplary embodiment of the current method and apparatus. Reusable or disposable cartridge 300 includes blades 324 and 326 and supporting dividers 330 positioned between the blades. FIG. 3B depicts a cross section of cartridge 300 of FIG. 3A at the level of blade 324 along axis Y-Y and viewed in the direction indicated by arrow (V). In this exemplary embodiment, blades 324 and 326 (not shown) are regular razor blades. Dividers 330 may be RF electrodes, or alternatively include RF electrodes on internal walls 330a and 330b thereof, and electrically communicate with RF generator 114 of handle 110 (FIG. 1).

The distance between adjacent dividers 330 may be predetermined according to the desired depth of heated portion 206 in skin 202 and level of coupled RF power as explained in detail hereinabove. Applying cartridge 300 against the skin to be shaved, urges the surface 302 of skin 202 against lip 328 of dividers 330, creating effective contact between the skin 202 and the dividers 330.

Coupling RF energy to skin 202 increases the temperature of the surface of the skin as well as the temperature of deeper skin tissue layers such as the dermis, the structures within the skin, and collagen layer as described hereinabove. Cooling the surface of the skin may increase the tolerance to the elevated temperature in the deeper layers and enhance the comfort of the shaving experience.

Figure 4A:
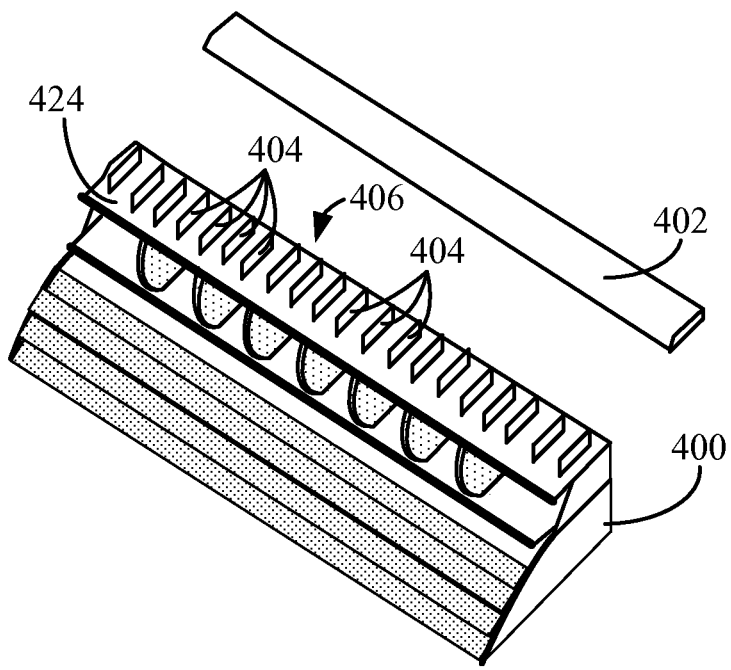
FIGS. 4A, 4B, 4C, 4D and 4E are simplified elevated oblique view and dropped oblique view and cross-sectional view illustrations of three additional exemplary embodiments of the shaving apparatus of the current method and apparatus.
Figure 4B:
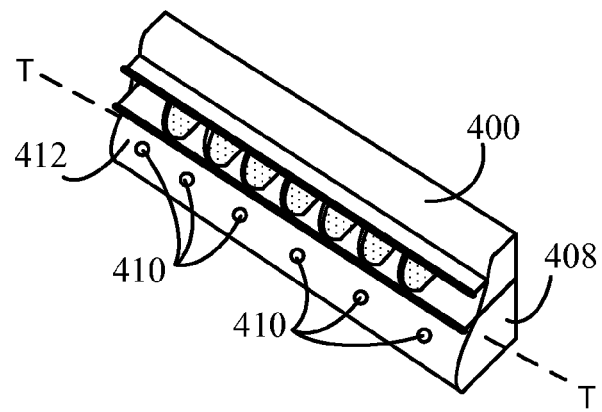

Turning now to FIGS. 4A and 4B, which are simplified elevated oblique view illustrations of an additional exemplary embodiment of the current method and apparatus. In FIG. 4A, which is a partially exploded view in which a blade cover portion 402 of a reusable or disposable cartridge 400 is raised for illustration purposes only to expose blade 424. Blade 424 may be forged with a multiplicity of projecting fins 404 constructed of a heat conducting material such as, but not limited to, copper or aluminum alloys and creating a heat sink 406 operative to dissipate heat conducted to blade 424 from the surface of the skin heated by RF energy.

Alternatively and additionally, blade 424 and heat sink 406 may be coated with a thermally conductive electrically insulating resin. In accordance with still another embodiment of the current method and apparatus, blade cover portion 402 may be made of a thermally conductive material embedding heat sink 406 when in place and attached to blade 424. FIG. 4B illustrates another embodiment of the current method and apparatus in which cartridge 400 further includes a conductive, cooling and hair softening gel dispenser 408 for dry skin shaving. Conductive, cooling and hair softening gel may be stored inside dispenser 408 and be applied to the skin through pores, openings, roller balls, or other applicators 410 at the application surface 412 thereof. Application surface 412 may be constructed of a semi-flexible material so that the gel may be applied through pores or openings 410 upon light squeezing pressure on dispenser 408 resulting from the pressing of cartridge 400 against the skin to be shaved.

Alternatively, the conductive, cooling and hair softening gel may be stored in a compartment (not shown) in handle 110 (FIG. 1) having a resilient wall and communicating through a dedicated detachable tube system with dispenser 408 and dispensed upon squeezing pressure applied to the gel compartment resilient wall by the user. Alternatively and additionally, the embodiments depicted in FIGS. 4A and 4B may be combined to add to the cooling effect of the gel to that of heat sink 406.

Figure 4C:
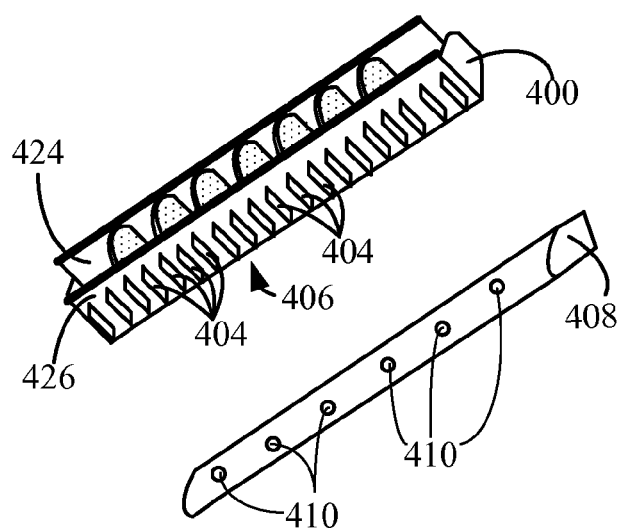
Figure 4E:
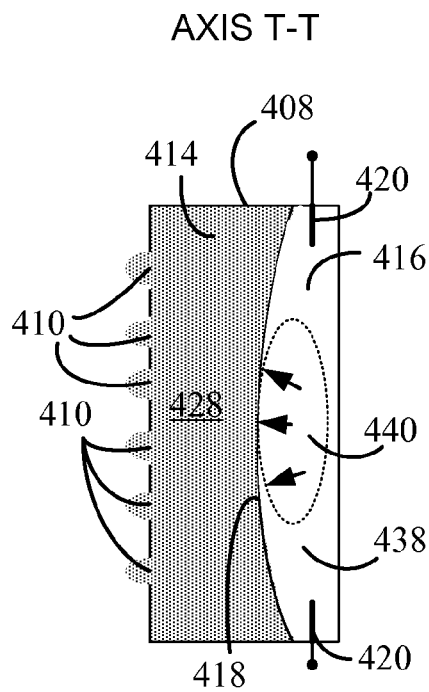
Figure 4D:
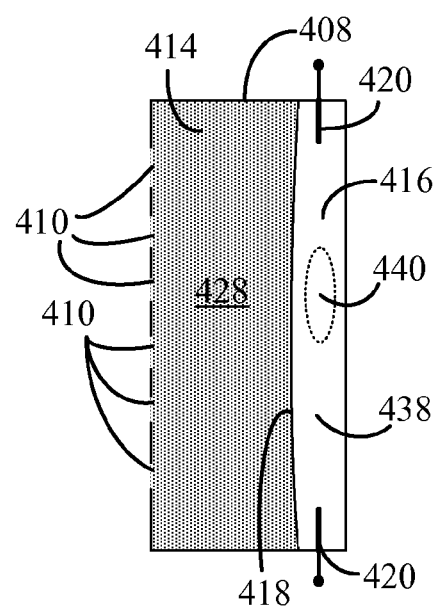

In FIG. 4C, which is a partially exploded dropped oblique view in which dispenser 408 is removed for illustration purposes only to expose blade 426. Blade 426 may be forged with a multiplicity of projecting fins 404 such as those depicted in FIG. 4A, constructed of a heat conducting material such as, but not limited to, copper or aluminum alloys and creating a heat sink 406. The heat conducted to blade 424 from the surface of the skin in this embodiment is conducted through blade 426 and heat sink 406 and heats the gel inside dispenser 408 (when attached) sufficiently to expand the volume of the gel urging it out through pores or openings 410. Alternatively, as depicted in FIGS. 4D and 4E, which are cross sectional view illustrations of FIG. 4B taken along axis T-T, dispenser 408 may include a first larger gel chamber 414 containing gel 428 and a second smaller fluid chamber 416 with a resilient divider 418 between the two chambers. Fluid chamber 416 further comprises heating electrodes 420, supplied by power source 112 in handle 110 and a fluid 438 with a high expansion coefficient. When switch 116 is activated, it also activates heating electrodes 420 that heat fluid 438 bringing about the boiling thereof creating a bubble 440. The expansion of bubble 440 in the direction indicated by the arrows urges against resilient divider 418 urging gel 428 out through pores or openings 410. The gel may be any water-based conductive gel, lubricant, moistener, etc. known in the art.

Figure 5A:
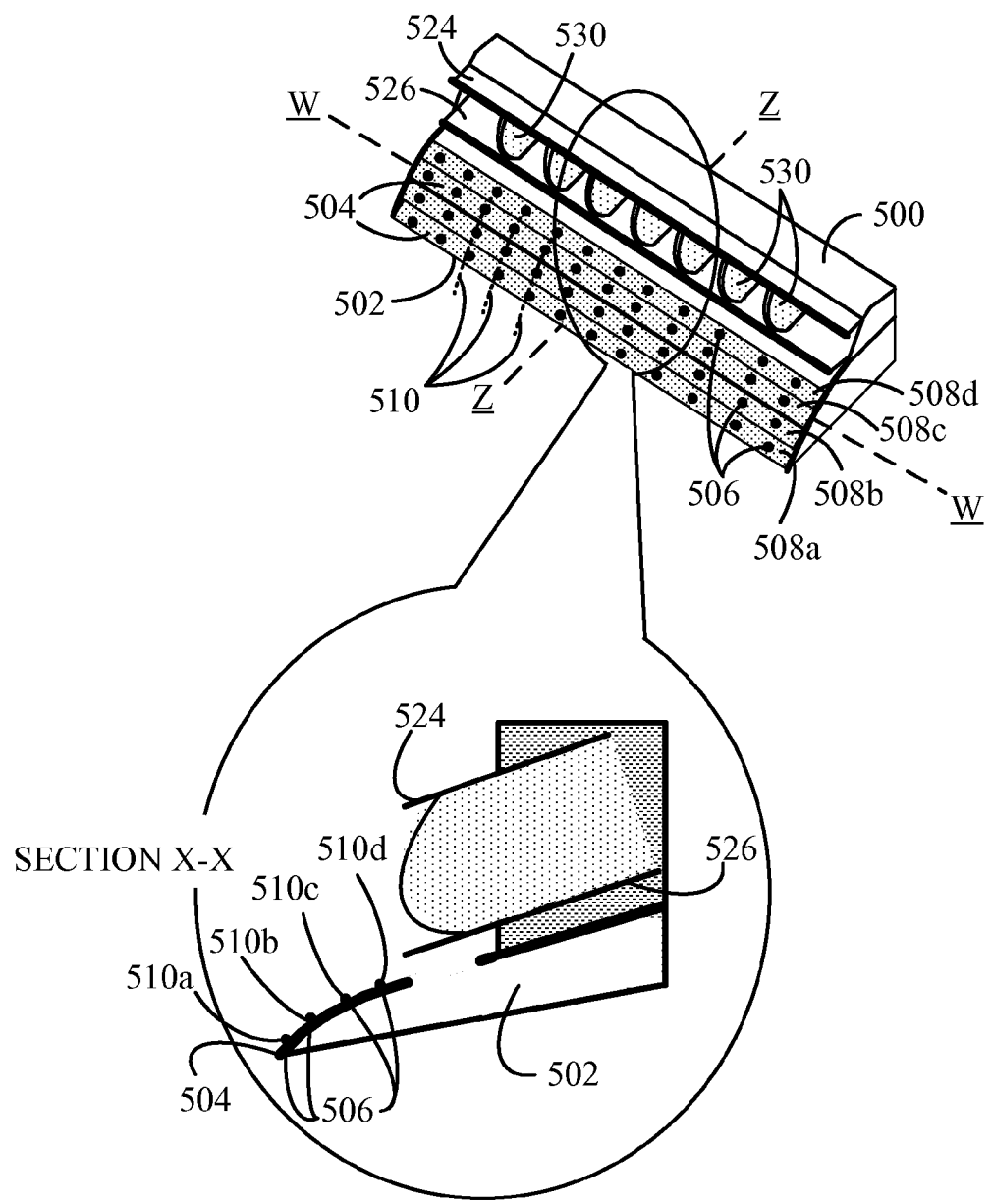

Referring now to FIG. 5A, which is a simplified elevated oblique view and sectional cross-section view illustration of another exemplary embodiment of the current method and apparatus. A reusable or disposable cartridge 500 includes blades 524 and 526 and supporting dividers 530 positioned between the blades. Additionally, cartridge 500 also includes a lip 502 that serves as an electrode carrier 504 for a multiplicity of RF voltage-applying dome-shaped elements 506 protruding from the surface thereof of the type described in assignee's above-incorporated by reference Patent Application No. WO2009/072108 and U.S. patent application Ser. No. 12/324,932.

Elements 506 may be arranged in lengthwise arranged rows 508a, 508b, 508c and 508d arranged along axes parallel to axis W-W. The electrical wiring of elements 506 may be configured to apply a current between all elements 506 sharing the same row and all elements 506 sharing an adjacent row. For example, an RF current may be applied between all elements sharing row 508a and all elements sharing row 508b and between all elements sharing row 508c and all elements sharing rows 508d. Since the depth of heated portion 206 in skin 202 is influenced by the distance between the electrodes and the current between them, the determination of which rows to apply RF energy to may depend on the desired depth of heated portion 206. This configuration is illustrated by FIG. 5B, which is a cross section of lip 502, carrier 504 and elements 506 in FIG. 5A taken along the axis Z-Z.

In accordance with yet another embodiment of the current method and apparatus, elements 506 may be arranged in crosswise arranged rows 510 (marked for the purpose of clarity by broken lines) arranged along axes parallel to axis Z-Z and wherein the electrical wiring of elements 506 applies a current between each pair of adjacent elements 506 sharing the same row. This configuration is illustrated by FIG. 5C, which is a cross section of carrier 504 and elements 506 in FIG. 5A taken along the axis W-W.

In accordance with still another embodiment of the current method and apparatus, any one of blades 524 or blade 526 may be operative to couple RF energy to skin or be replaced by an RF electrode. A current may be applied between all, a single row or multiple rows of elements 506 on carrier 504 and blade 524 or 526. It will be appreciated that the distance between elements 506 and blade 524 or 526 will determine the depth of heated portion 206 of skin 202 from the surface thereof. Voltage may be applied, for example, between all, a single row or multiple rows of elements 506 on carrier 504 and blade 526. This configuration is similar to the configuration depicted in FIGS. 2C, 2D and 2E. Additionally, electrode carrier 504 may also include a thermistor 512 being in contact with the surface of skin 202 for skin temperature control. It will also be appreciated that a series of switches may be included in the control circuitry so that the application of the RF energy can be dynamically changed and controlled during the use of the device. For instance, the switches can be open or closed thereby changing the flow of the RF energy between the various electrodes and blades. Such control can be random, sequenced, based on feedback, or any of a variety of other criteria.

Figure 6:
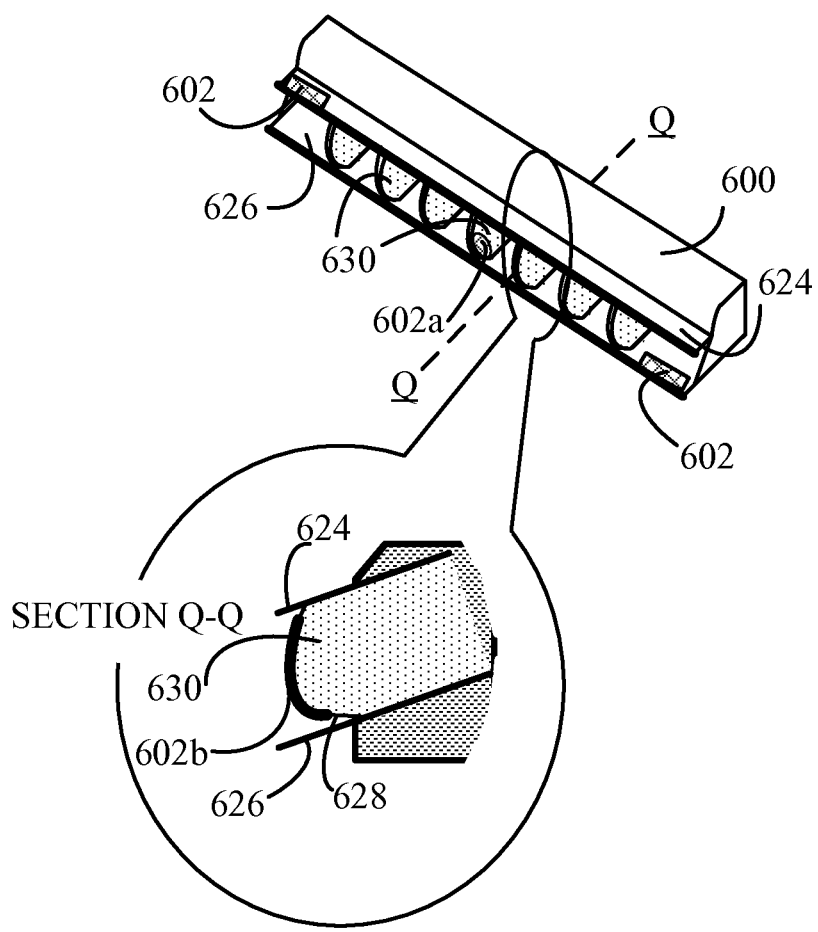
FIG. 6 is a simplified elevated oblique view and cross-sectional view illustration of another embodiment of the current method and apparatus.

Turning now to FIG. 6, which is a simplified elevated oblique view illustration of another embodiment of the current method and apparatus. A reusable or disposable cartridge 600 includes one or more thermistors 602 which may supply feedback to circuit controller 116 to modify RF energy application in accordance with the temperature of the skin surface and to avoid overheating of the skin thus contributing to the safety and comfort of shaving. FIG. 600 depicts several possible locations for placing such thermistors 602, such as on blades 624 and/or 626, sidewalls of divider 630 as designated by reference numeral 602a or along lip 628 of dividers 630 as designated by reference numeral 602b to make contact with the surface of skin 202 while shaving. Additionally or alternatively, thermistors 602 may also be placed in any other desired suitable location.

In an exemplary embodiment, a controller/charger base may be included with the shaving apparatus. In such an embodiment, the control of the RF circuitry and the charging of batteries within the shaving apparatus may be incorporated into the base. The base and the shaver may include a wireless communication means, such as BLUETOOTH for providing control of the RF control and/or receiving feedback from the thermistors, battery level, etc. For example, in such an embodiment, the base may be used to receive temperature feedback from one or more thermistors and, then provide control of the application of RF energy by sending control commands to the shaving device.

It will be appreciated that the energy applied by the aforementioned electrodes may be replaced in the future by other heating energy generating means such as laser energy, ultraviolet (UV) commonly used in treatment of acne, ultrasound energy, and others.

It will also be appreciated by persons skilled in the art that the present method and apparatus are not limited to what has been particularly shown and described hereinabove. Rather, the scope of the method and apparatus includes both combinations and sub-combinations of various features described hereinabove as well as modifications and variations thereof which would occur to a person skilled in the art upon reading the foregoing description and which are not in the prior art.

What is claimed is:

1. A shaving apparatus, said apparatus comprising:
a cartridge to be applied to the skin including at least one blade; a source of RF energy operative to supply RF energy to said blade; and a handle that can be coupled to said cartridge and operative to enable the translation of said cartridge over the skin such that at least one blade is operative to couple RF energy at a frequency in the range of 300 KHz to 10 MHz to the skin and engage hair on the surface of the skin during shaving.

2. The apparatus according to claim 1, wherein said cartridge comprises at least two blades arranged in parallel orientation to each other.

3. The apparatus according to claim 2, wherein the two blades couple RF energy to the skin.

4. The apparatus according to claim 2, wherein at least one of said blades includes a temperature sensor.

5. The apparatus according to claim 2, wherein said cartridge further comprises a temperature sensor operative to contact the surface of the skin.

6. The apparatus according to claim 5, wherein said sensor is located between said blades.

7. The apparatus according to claim 1, further comprising at least one power supply operative to power said source of RF energy and heat said blades.

8. The apparatus according to claim 1, wherein said cartridge is a disposable cartridge.

9. A shaving apparatus, said apparatus comprising:
a cartridge to be applied to the skin including at least one blade operative to engage with hair on the skin and at least one electrode operative to couple RF to a target segment of the skin;
a source of RF energy coupled to and operative to supply RF energy to the skin during shaving at a frequency in the range of 300 KHz to 10 MHz to said electrode; and
a handle attachable to said cartridge and operative to enable the translation of said cartridge over the skin.

10. The apparatus according to claim 9, further comprising at least two electrodes and wherein the at least one blade is located between the electrodes, the electrodes and at least one blade arranged within the cartridge to be applied to the skin and are in parallel to each other.

11. The apparatus according to claim 9, further comprising at least two electrodes and wherein said cartridge further comprises a temperature sensor located between said electrodes and operative to contact the surface of the skin.

12. The apparatus according to claim 9, wherein said at least one blade includes a temperature sensor.

13. The apparatus according to claim 9, wherein said at least one said electrode includes a temperature sensor.

14. The apparatus according to claim 9, further comprising at least one power supply operative to power said source of RF energy and heat the blades.

* * * * *